(12) United States Patent
Burger et al.

(10) Patent No.: US 9,198,856 B2
(45) Date of Patent: Dec. 1, 2015

(54) FORMULATION FOR STABILIZING PROTEINS, WHICH IS FREE OF MAMMALIAN EXCIPIENT

(75) Inventors: Markus Burger, Frankfurt am Main (DE); Gerd J. Mander, Frankfurt am Main (DE); Harold Victor Taylor, Frankfurt am Main (DE)

(73) Assignee: MERZ PHARMA GmbH & CO. KGaA, Frankfurt am Main (DE)

( * ) Notice: Subject to any disclaimer, the term of this patent is extended or adjusted under 35 U.S.C. 154(b) by 0 days.

(21) Appl. No.: 13/138,884

(22) PCT Filed: Apr. 16, 2010

(86) PCT No.: PCT/EP2010/002360
§ 371 (c)(1),
(2), (4) Date: Dec. 30, 2011

(87) PCT Pub. No.: WO2010/118888
PCT Pub. Date: Oct. 21, 2010

(65) Prior Publication Data
US 2012/0093866 A1 Apr. 19, 2012

Related U.S. Application Data

(60) Provisional application No. 61/212,952, filed on Apr. 17, 2009.

(30) Foreign Application Priority Data

Apr. 17, 2009 (EP) .................................... 09005470

(51) Int. Cl.
| | |
|---|---|
| A61K 39/08 | (2006.01) |
| A61K 9/00 | (2006.01) |
| A61K 8/34 | (2006.01) |
| A61K 8/60 | (2006.01) |
| A61K 8/64 | (2006.01) |
| A61K 8/73 | (2006.01) |
| A61K 8/86 | (2006.01) |
| A61K 9/08 | (2006.01) |
| A61K 9/19 | (2006.01) |
| A61K 38/48 | (2006.01) |
| A61K 47/14 | (2006.01) |
| A61K 47/26 | (2006.01) |
| A61K 47/32 | (2006.01) |
| A61K 47/36 | (2006.01) |
| A61Q 19/00 | (2006.01) |

(52) U.S. Cl.
CPC .............. *A61K 9/0019* (2013.01); *A61K 8/345* (2013.01); *A61K 8/60* (2013.01); *A61K 8/64* (2013.01); *A61K 8/735* (2013.01); *A61K 8/86* (2013.01); *A61K 9/08* (2013.01); *A61K 9/19* (2013.01); *A61K 38/4893* (2013.01); *A61K 47/14* (2013.01); *A61K 47/26* (2013.01); *A61K 47/32* (2013.01); *A61K 47/36* (2013.01); *A61Q 19/00* (2013.01); *A61K 2800/91* (2013.01)

(58) Field of Classification Search
CPC ......... A61K 8/345; A61K 8/64; A61K 8/735; A61K 8/86; A61K 9/0019; A61K 9/08; A61K 9/19; A61K 38/4893; A61K 47/14; A61K 47/26; A61K 47/32; A61K 47/36; A61K 2800/91; A61K 8/60; A61Q 19/00
See application file for complete search history.

(56) References Cited

U.S. PATENT DOCUMENTS

| | | | |
|---|---|---|---|
| 5,955,105 | A | 9/1999 | Mitra et al. |
| 6,447,806 | B1 | 9/2002 | Gassmann et al. |
| 7,247,707 | B2 | 7/2007 | Besman et al. |
| 2006/0018931 | A1* | 1/2006 | Taylor ........................ 424/239.1 |
| 2007/0122476 | A1* | 5/2007 | Hanshew et al. ............. 424/464 |
| 2007/0134199 | A1 | 6/2007 | Frevert |
| 2007/0154493 | A1* | 7/2007 | Hattendorf et al. ........ 424/239.1 |
| 2009/0155314 | A1 | 6/2009 | Tezel et al. |
| 2010/0279953 | A1* | 11/2010 | Hunt ........................... 514/21.2 |

FOREIGN PATENT DOCUMENTS

| | | |
|---|---|---|
| FR | 2881139 | 7/2006 |
| JP | 2004 043475 | 2/2004 |
| JP | 2007-537274 | 12/2007 |
| JP | 2008-507581 | 3/2008 |
| WO | WO 00/74703 | 12/2000 |
| WO | WO 01/58472 | 8/2001 |
| WO | WO 2004/006954 | 1/2004 |
| WO | WO 2006/005910 | 1/2006 |
| WO | WO 2006/027207 | 3/2006 |
| WO | WO 2006/079722 | 8/2006 |
| WO | WO 2006/114308 | 11/2006 |
| WO | WO2007041664 A | 4/2007 |
| WO | WO 2009/008595 | 1/2009 |
| WO | WO 2009/015840 | 2/2009 |

OTHER PUBLICATIONS

Carpenter, et al., Pharmaceutical Biotechnonogy, vol. 13, p. 109,133, Jan. 2002.
European Search Report With Written Opinion for EP09005470 of Oct. 12, 2009.
Goschel, et al, Experimental Neurology, vol. 147, p. 96-102, 1997.
International Search Report With Written Opinion for PCT/FR2010/002360 of May 19, 2010.
Montecucco C., et al., Arch Toxicol. vol. 18 (suppl.), p. 342-354, 1996.
Rompp Chemie Lexikon, 9.Auflage (1995), Thieme Verlag, p. 5165, Right column.
Simpson L.L., Annu. Rev. Pharmaxological Toxicology. vol. 44, p. 167-193, 2004.
Office Action, Chinese Application No. 201080016257.6, Oct. 23, 2012. (Chinese Language).
Office Action, Chinese Application No. 201080016257.6 Oct. 23, 2012, (English Language Translation).
Office Action dated Feb. 14, 2014 from corresponding Russian application No. 201146541/15(069722).
Office Action dated Jan. 7, 2014 from corresponding Japanese application 2012-505092 with English translation.
Office Action dated Jan. 23, 2014 from corresponding Chinese application 201080016527.6 with English translation.

* cited by examiner

*Primary Examiner* — Suzanne Ziska
(74) *Attorney, Agent, or Firm* — Hueschen and Sage

(57) ABSTRACT

The present invention pertains to a formulation comprising a hydrophilic polymer, a mixture of a polyalcohol and a sugar, wherein the weight ratio of polyalcohol to sugar is between 2:1 to 5:1 (wt-%), a detergent, and wherein the formulation is free of stabilizing proteins.

9 Claims, No Drawings

FORMULATION FOR STABILIZING PROTEINS, WHICH IS FREE OF MAMMALIAN EXCIPIENT

FIELD OF THE INVENTION

The present invention pertains to a formulation for stabilizing proteins, which is free of mammalian excipients. In particular, it pertains to a formulation comprising a hydrophilic polymer, a mixture of a polyalcohol and a sugar, wherein the weight ratio of polyalcohol to sugar is from 2:1 to 5:1 (wt-%), a detergent, and wherein the formulation is free of stabilising proteins. In one embodiment, the present invention pertains to a kit, wherein said kit comprises one or more containers comprising the said formulation/composition, instructions for use and optionally, a pharmaceutically acceptable sterile solvent.

BACKGROUND OF THE INVENTION

Protein formulations, which are free of stabilizing proteins are known in the art. WO 2006/020208 relates to pharmaceutical compositions comprising Botulinum toxin and a non-proteinaceous stabilizing agent, which retains the activity of the Botulinum toxin in an aqueous solution.

WO 2006/005910 relates to solid or liquid pharmaceutical compositions comprising Botulinum toxin complex or high purity Botulinum toxin and a surfactant. A maximum of six months stability at 23° C. to 27° C. is reported therein.

WO 2007/041664 relates to a pharmaceutical composition comprising a Botulinum toxin and a polyvinylpyrollidone (PVP) and optionally a disaccharide.

WO 2004/006954 relates to a pharmaceutical composition comprising a stabilized Botulinum toxin and at least one enhancing agent for facilitating transdermal delivery of the Botulinum toxin into a human patient by enhancing the permeability of the patient's skin.

WO 01/58472 discloses a pharmaceutical composition suitable for injection into a human patient, comprising a Botulinum toxin and a polysaccharide. It also discloses a pharmaceutical composition comprising a neurotoxin and hydroxyethyl starch.

WO 2006/079722 relates to the use of liquid compositions for implementing the method of freeze-drying proteins, to stabilize said proteins, said compositions comprising; a filler agent having a collapse temperature between −18° C. and 0° C., a stabilizer, a buffer solution, and, as the case may be, a nonionic surfactant.

OBJECTS OF THE INVENTION

An object of the present invention was to provide a novel formulation for stabilizing proteins, which is free of stabilizing proteins. Such formulations may be formulated such that they provide superior stability to proteins, compared to formulations of the prior art.

This and other objects were achieved by the formulation being the subject of this application.

SUMMARY OF THE INVENTION

The objects of the invention were achieved by the formulation being subject of this application. The present invention pertains to a formulation comprising a hydrophilic polymer, a mixture of a polyalcohol and a sugar, wherein the weight ratio of polyalcohol to sugar is from [2:1] to [5:1] (wt-%), e.g. [2:1], [2.5:1], [3:1], [3.5:1], [4:1], [4.5:1], [5:1], a detergent, and wherein the formulation is free of stabilising proteins. In one further embodiment, the present invention pertains to a composition that comprises the said formulation and a peptide, a protein or a mixture thereof, naturally occurring or modified/artificial.

In one further embodiment the composition of the invention is lyophilised.

A further aspect of the present invention relates to a composition comprising a peptide or a protein, or a mixture thereof, as defined herein, for use as a medicament, a cosmetic product, a cosmoceutical product or a diagnostic product.

One further aspect of the present invention relates to said composition for use in the treatment of a disease or condition caused by or associated with hyperactive cholinergic innervation of muscles or exocrine glands in a patient.

A further aspect of the present invention relates to a kit comprising one or more of a container comprising said formulation/composition and instructions for use of the said formulation and optionally a pharmaceutically acceptable sterile solvent.

DETAILED DESCRIPTION OF THE INVENTION

The present invention pertains to a formulation comprising a hydrophilic polymer, a mixture of a polyalcohol and a sugar, wherein the weight ratio of polyalcohol to sugar is between [2:1] to [5:1] (wt-%), e.g. [2:1], [2.5:1], [3:1], [3.5:1], [4:1], [4.5:1], [5:1], a detergent, and wherein said formulation is free of stabilising proteins.

The term "formulation" as used herein relates to a mixture comprising pharmaceutically acceptable excipients and encompasses liquid, solid, semisolid, colloidal and all other forms known to the person skilled in the art. The said formulation herein is free of stabilizing proteins.

The term "composition" as used in the instant invention relates to a formulation as claimed herein which further comprises a peptide, a protein or a mixture thereof.

The formulation of the invention comprises a hydrophilic polymer.

The term "polymer" as used herein relates to structures composed of repeating units. The term "polymer" within the scope of the instant invention is employed both for homopolymers and copolymers.

The term "hydrophilic" as used herein relates to substances, materials, excipients or pharmaceutically active ingredients which are wettable by water.

In one embodiment of the present invention, the hydrophilic polymer is selected from the group consisting of hyaluronic acid, polyvinylpyrollidone (PVP), copolymers of N-vinylpyrollidone, cellulose derivatives, Polyethyleneglycol (PEG), PEG/PPG block copolymers, homo- and copolymers of acrylic and methacrylic acid, polyurethanes, polyvinyl alcohol (PVA), polyvinylethers, maleic anhydride based copolymers, polyesters, vinylamines, polyethyleneimines, polyethyleneoxides, poly(carboxylic acids), polyamides, polyanhydrides, polyphosphazenes and mixtures thereof.

The said cellulose derivative may be selected from the group consisting of hydroxypropyl methyl cellulose, hydroxypropyl cellulose, hydroxyethyl cellulose, methyl cellulose, carboxymethyl cellulose, dextran, and mixtures thereof.

The term "Polyvinylpyrrolidone" as used herein refers to a water-soluble polymer made from the monomer N-vinylpyrrolidone. The terms and abbreviations "PVP, povidone, polyvidone, crospovidone, Kollidone" are used synonymously.

The said polyvinylpyrrollidone (PVP) may be Kollidon 12 PF, Kollidon 17 PF, Kollidon 25, Kollidon 30, Kollidon 90 F, povidone, crospovidone, Kollidon VA 64 and copovidone or a mixture thereof.

The term "hyaluronic acid" within the meaning of the instant invention refers to a non-sulfated glycosaminoglycan. In one embodiment the hyaluronic acid has a molecular weight of 0.8 to $1.2 \times 10^6$ Da. Furthermore, within the present invention also crosslinked hyaluronic acid may be used. The term "hyaluronic acid" is used synonymously with the term "hyaluronan". Within the present invention the term "hyaluronic acid" also encompasses derivatives of hyaluronic acid, such as salts thereof, e.g. sodium, potassium, magnesium and calcium salts. Further the term "hyaluronic acid" encompasses all natural and synthetic derivates thereof. It is a molecule having typically a molecular weight of 10 kDa and $4.5 \times 10^6$ Da.

The formulation of the invention comprises a mixture of polyalcohol and sugar in a weight ratio of from [2:1] to [5:1] (wt. %).

The term "polyalcohol" as used herein relates to a group of carbohydrate-based ingredients, which are employed to protect the protein against instability. The term "polyol" and "sugar alcohols" are used synonymously.

The term "sugar" as used herein relates to any monosaccharide, disaccharide and polysaccharide. The term "monosaccharide" as used herein relates to the basic units of carbohydrates. The term "disaccharide" within the scope of the present invention relates to carbohydrates composed of two monosaccharides. The term "polysaccharides" as used herein relates to repeating units of monosaccharides, wherein the monosaccharides are bound with glycosidic bonds.

The term "mixture" as used herein relates to compositions of homogeneous or heterogeneous nature, wherein at least two substances of the same or different composite or structure are mixed by employing the methods and devices known to the person skilled in the art. The term "mixture" within the scope of the instant invention encompasses mixtures in solid, liquid and semisolid form.

The term "mixing" as used herein relates to combining at least two active or inactive ingredients at various proportions. Mixing relates to any process or action which combines also at least two different active or inactive substances from the same group or from different groups, in any sequential order. The term "mixing" also discloses any process or action which combines any active ingredient with any excipient.

In one embodiment of the present invention the polyalcohol is selected from the group consisting of mannitol, inositol, lactilol, isomalt, xylitol, erythritol and sorbitol.

In one further embodiment of the present invention the sugar is selected from the group consisting of monosaccharides, wherein said monosaccharides may be glucose, thioglucose, thiomannose, thiofructose, fructose and galactose. In another embodiment the sugar is a disaccharide, wherein said disaccharide may be trehalose, sucrose, octa-O-acetylthiotrehalose, thiosucrose, thiomaltose, maltose, and maltitol. In one further embodiment the sugar is a polysaccharide, wherein said polysaccharide may be an alginate, hydroxyethyl starch and hydroxypropyl starch.

The present invention claims a formulation, wherein a polyalcohol and a sugar are mixed to obtain a mixture of polyalcohol and sugar at a weight ratio of [2:1] to [5:1]. In one further embodiment said mixture of polyalcohol and sugar is at a weight ratio of [2:1] to [3:1], e.g. [2:1], [2.5:1], [3:1]. In another embodiment said mixture of polyalcohol and sugar is at a weight ratio of [3:1].

According to one embodiment of the instant invention the mixture of polyalcohol and sugar comprises mannitol and sucrose at a weight ration of [2:1] to [5:1], e.g. [2:1], [2.5:1], [3:1], [3.5:1], [4:1], [4.5:1], [5:1]. In one further embodiment of the instant invention the mixture of polyalcohol and sugar comprises mannitol and sucrose at a weight ration of [3:1].

Said polyalcohol and said sugar may be mixed by using V-blenders (twin shell blenders), rotary drum mixers, double ribbon blenders, plow mixers, paddle mixers, double cone blenders. The skilled person will be able to select the correct mixer depending on bench-top scale or high scale. The mixing time will depend on the batch size, quality of excipients, e.g. particle size of the powder and the mixer type.

The formulation of the invention also comprises a detergent.

The term "detergent" as used herein relates to any substance employed to solubilize or stabilize another substance, which may be either a pharmaceutical active ingredient or another excipient in a formulation. Said detergent may stabilize said protein or peptide either sterically or electrostatically. The term "detergent" is used synonymously with the terms "surfactants" or "surface active agents".

In one embodiment of the present invention the detergent is selected from the group consisting of non-ionic surfactants.

The term "non-ionic surfactants" within the meaning of the instant invention refers to surfactants having no positive or negative charge.

According to one aspect said non-ionic surfactants may be sorbitan esters (sorbitan monolaurate, sorbitan monopalmitate, sorbitan monostearate, sorbitan tristearate, sorbitan monooleate, Sorbitan trioleate), polysorbates (polyoxyethylene (20) sorbitan monolaurate (Polysorbate 20), polyoxyethylene (20) sorbitan monopalmitate, polyoxyethylene (20) Sorbitan monostearate, polyoxyethylene (20) sorbitan tristearate, polyoxyethylene (20) Sorbitan trioleate, Polyoxyethylen (20)-sorbitan-monooleate (Tween 80/Polysorbate 80)), poloxamers (poloxamer 407, poloxamer 188), cremophor, and mixture thereof.

In another embodiment said detergent is anionic surfactant.

The term "anionic surfactant" within the meaning of the present invention refers to surfactants comprising an anionic hydrophilic group.

According to one aspect said anionic surfactant may be tetradecyltrimethylammonium bromide, dodecyltrimethylammonium bromide, sodium laureth sulphate, sodium dodecyl sulphate (SDS), cetrimide, hexadecyltrimethylammonium bromide, and a mixture thereof.

In one further embodiment said detergent is a cationic surfactant.

The term "cationic surfactant" within the meaning of the instant invention encompasses surfactants comprising an cationic hydrophilic group.

According to one aspect said cationic surfactant may be benzalkonium chloride, cetyl trimethlammonium bromide (CTAB), cetylpyridinium chloride (CPC), benzethonium chloride (BZT), and mixtures thereof.

In one embodiment of the present invention the concentration of the detergent is not more than 0.5 mg/g based on the total weight of the production bulk composition, i.e. the total amount of the formulation of the invention, the peptide or protein to be stabilized and the sterile solvent added for injection, typically water or an isotonic saline solution. In one further embodiment of the instant invention, the concentration of the detergent is between 0.1 mg/g and 0.3 mg/g based on the total weight of the production bulk composition. In another embodiment of the instant invention the detergent employed is Polysorbate 80 and the concentration thereof is 0.2 mg/g based on the total weight of the production bulk composition.

The term "production bulk composition" as used herein refers to the composition existing prior to filling of the composition into individual dosing units.

In one embodiment of the instant invention the hydrophilic polymer employed is hyaluronic acid and the detergent employed is Polysorbate 80.

In one further embodiment of the present invention the hydrophilic polymer employed is hyaluronic acid and the detergent employed is Polysorbate 20.

In one further embodiment of the present invention the hydrophilic polymer employed is polyvinylpyroldone (PVP) and the detergent employed is Polysorbate 80.

The formulation of the invention is free of stabilising proteins.

The term "free of stabilising proteins" within the meaning of the present invention refers to formulations being free of peptides or proteins that stabilize the active peptide or protein. Examples for such excipients are, but not limited to, human serum albumin (HSA), gelatine, amino acids such as histidine, lysine, methionine or immunoglobulins.

The formulation of the instant invention is used for stabilising proteins, peptides, or mixtures thereof.

The present invention further pertains to a composition comprising said formulation and an active agent which may be a protein, a peptide, naturally occurring or modified/artificial or a mixture thereof The term "stable composition" as used herein relates to a composition, wherein the protein or peptide retains upon storage for at least 4 weeks at room temperature, 60% RH its physical and chemical stability and integrity up to 50%, 60%, 70%, 80% and 90% compared to the value measured after lyophilisation, meaning prior to storage.

In a further embodiment, the composition of the invention is composed such that the protein or peptide retains upon storage for at least 6 months at room temperature, 60% RH its physical and chemical stability and integrity up to 50%, 60%, 70%, 80% and 90% compared to the value measured after lyophilisation, meaning prior to storage.

In a still further embodiment, the composition of the invention is composed such that the protein or peptide retains upon storage for at least 12 months at room temperature, 60% RH its physical and chemical stability and integrity up to 50%, 60%, 70%, 80% and 90% compared to the value measured after lyophilisation, meaning prior to storage.

As to the biological activity, "stable composition" refers to a composition, wherein the neurotoxic component in a reconstituted or aqueous solution of pharmaceutical composition has greater than about 20%, 30%, 40%, 50%, 60%, 70%, 80%, 90%, and up to about 100% of the toxicity that the biologically active neurotoxic component had prior to being incorporated into the pharmaceutical composition.

The term "room temperature" also designated as RT (or ambient temperature) within the meaning of the instant invention, refers to the definition of U.S. Pharmacopeia as being 20-25° C. [68-77° F.].

The term "relative humidity" also designated as RH within the meaning of the instant invention, refers to the ratio of the amount of water vapor in the air at a specific temperature to the maximum amount that the air could hold at that temperature, expressed as a percentage.

In one aspect of the invention said composition herein is stable for 7 months at 25° C. and 60% RH in lyophilised form. In another aspect of the invention said composition is stable for 3 months at 25° C. and 60% RH in lyophilised form. In one further aspect of the invention said composition is stable for 2 months at 25° C. and 60% RH in lyophilised form. In another aspect of the invention said composition is stable for 1 month at 25° C. and 60% RH in lyophilised form.

In another aspect of the invention said composition is stable for 7 months at 40° C. and 75% RH as in lyophilised form. In one further aspect of the invention said composition is stable for 3 months at 40° C. and 75% RH in lyophilised form. In one further aspect of the invention said composition is stable for 2 months at 40° C. and 75% RH in lyophilised form. In one further aspect of the invention said composition is stable for 1 month at 40° C. and 75% RH in lyophilised form.

In one embodiment of the instant invention the stability is measured by measuring the extent of aggregation as a function of time as an indicator of protein stability. In another embodiment, stability of the protein composition may be measured using the analytical methods known to the one skilled in the art by determining % of intact protein, e.g. proteolytic cleavage, cell based assay. In one further embodiment the stability of the protein composition was determined by employing a Mouse-hemidiaphragm assay (HDA-assay). In one embodiment of the instant invention HDA-assay is employed to determined the stability of the compositions claimed herein. The results are demonstrated as the potency measured in an HDA assay.

The HDA-Assay is conducted as defined by Göschel et al. ("*Botulinum* Toxin Therapy: Neutralizing and Nonneutralizing Antibodies—Therapeutic Consequences" Experimental Neurology, 1997; 147: 96-102).

The instant invention further pertains to a composition that comprises the said formulation and a peptide, a protein or a mixture thereof, being naturally occurring or modified/artificial. Modification comprises chemical modification e.g. by glycosylation, acetylation, acylation or the like, which may be beneficial e.g. to the uptake or stability of the protein. The polypeptide chain of the protein may, however, alternatively or additionally be modified by addition, substitution or deletion of one or more amino acid residues.

The term "peptide" within the meaning of the present invention refers to short polymers formed by linking in a defined order of alpha-amino acids.

The term "protein" as used herein relates to compounds of amino acids arranged in a linear chain and joined together by peptide bonds between the carboxyl and amino groups of adjacent amino acid residues. The term "protein" is used synonymously with the term "polypeptide". Proteins according to the instant invention may be artificial or naturally occurring.

The active protein or peptide in the formulation claimed herein may be artificial/modified or naturally occurring.

The term "artificial protein" within the meaning of the present invention refers to modified proteins. The term "modified protein" encompasses all possible modifications known to the person skilled in the art, e.g. chemical modification, deletion.

The term "naturally occurring" within the meaning of the present invention refers to proteins or peptides found naturally in mammal organism.

In one embodiment of the present invention, said protein is selected from the group consisting of toxins, chondroitin, elastin, actin, myosin, aprotinin, growth hormone, growth hormone releasing factor, parathyroid hormone, thyroid stimulating hormone, lipoproteins (LDL, IDL, VLDL, VHDL, HDL), apolipoproteins (ApoA-1, ApoA-II, ApoA-IV, ApoC-I, ApoC-II, ApoC-III, ApoD, ApoE), α-1 Antitrypsin, insulin, proinsullin, follicle stimulating hormone, calcitonin, oxytocin, vasopressin, leuprolide acetate, somatostatin, luteinizing hormone, glucagons, clotting factors, anti-clotting factors, plasminogen activator, human macrophage inflammatory protein, vascular endothelin growth factor (VEGF), rheumatoid factors, bone derived neurotrophic factor (BDNF), nerve growth factor-β (NGF-β), platelet-derived growth factor (PDGF), fibroblast growth factor (FGF), epidermal growth factor (EGF), transforming growth factor (TGF-β1, TGF-β2, TGF-β3, TGF-β4, TGF-β5), erythropoietin, interleukins (IL-1 to IL-10), bone morphogenic protein (BMP) parathyroid hormone, DNAse, cationic ferritin, interferon (α, β, γ) and mixtures thereof.

In another embodiment of the present invention said protein is a toxin. In one further embodiment of the instant invention said toxin is, a *Botulinum* toxin, a diphtheria toxin or a tetanus toxin, or a mixture of two or more thereof.

In one embodiment of the present invention the protein in the said composition is *Botulinum* toxin.

In one further embodiment of the instant invention said *Botulinum* toxin is selected from the group consisting of type A, B, C, $C_1$, D, E, F and G. In another embodiment of the present invention said *Botulinum* toxin is type A. In one further embodiment of the instant invention said protein is the neurotoxic component of *Botulinum* toxin type A.

The term "*Botulinum* toxin" as used throughout the present application, refers to the neurotoxic component devoid of any other Clostridial proteins, but also to the "*Botulinum* toxin complex". The term "*Botulinum* toxin" is used herein in cases when no discrimination between the toxin complex and the neurotoxic component is necessary or desired. "BoNT" or "NT" are commonly used abbreviations.

The "neurotoxic component" of the *Botulinum* toxin complex is initially formed as a single polypeptide chain, having in the case of serotype A a molecular weight of approximately 150 kDa. In other serotypes the neurotoxic component has been observed to vary between about 145 and about 170 kDa, depending on the bacterial source. In the case of serotype A, for example, proteolytic processing of the polypeptide results in an activated polypeptide in the form of a dichain polypeptide consisting of a heavy chain and a light chain, which are linked by a disulfide bond. In humans, the heavy chain mediates binding to pre-synaptic cholinergic nerve terminals and internalization of the toxin into the cell. The term "neurotoxic component" also includes functional homologs found in the other serotypes of *Clostridium botulinum*. In one embodiment of the present invention, the neurotoxic component is devoid of any other *C. botulinum* protein, e.g. also devoid of RNA, which might potentially be associated with the neurotoxic component. The neurotoxic component may be the single chain precursor protein of approximately 150 kDa or the proteolytically processed neurotoxic component, comprising the light chain (Lc) of approximately 50 kDa and the heavy chain (Hc) of approximately 100 kDa, which may be linked by one or more disulfide bonds (for a review see e.g. Simpson L L, Ann Rev Pharmacol Toxicol. 2004; 44:167-93). In humans, the heavy chain mediates binding to pre-synaptic cholinergic nerve terminals and internalization of the toxin into the cell. The light chain is believed to be responsible for the toxic effects, acting as zinc-endopeptidase and cleaving specific proteins responsible for membrane fusion (SNARE complex) (see e.g. Montecucco C., Shiavo G., Rosetto O: The mechanism of action of tetanus and *Botulinum* neurotoxins. Arch Toxicol. 1996; 18 (Suppl.): 342-354)).

The neurotoxic subunit of the *Botulinum* toxin complex is referred in this document as the "neurotoxic component" or the "neurotoxic component free of complexing proteins". The production of the neurotoxic component of *Botulinum* toxin type A and B are described, for example, in the international patent application WO 00/74703.

In a further embodiment the *Botulinum* toxin is *Botulinum* toxin type A. In one embodiment said *Botulinum* toxin is free of any complexing proteins (neurotoxic component). In one further embodiment it is the pure neurotoxic component serotype A. In addition thereto, modified as well as recombinant produced neurotoxic components of *Botulinum* toxins including the respective mutations, deletions, etc. are also within the scope of the present invention. With respect to suitable mutants, reference is made to WO 2006/027207 A1, WO 2009/015840 A1, WO 2006/114308 A1 and EP 08015287.9 which are fully incorporated by reference herein. Furthermore, within the present invention, mixtures of various serotypes (in the form the neurotoxic component or recombinant form or both forms thereof, e.g. mixtures of *Botulinum* neurotoxins of types A and B) may be used. The present invention, however, also refers to toxins, e.g. *Botulinum* toxins, which are chemically modified, e.g. by pegylation, glycosylation, sulfatation, phosphorylation or any other modification, in particular of one or more surface or solvent exposed amino acid(s). Such *Botulinum* toxins are disclosed in e.g. EP 08015288.7 and the prior art disclosed therein.

In accordance with the teaching of the present invention, it also encompasses that the medicament contains no proteins found in the *Botulinum* toxin complex other than the neurotoxic component.

The *Botulinum* toxin, preferably the neurotoxic component referred to herein, may be the sole active component or may contain additional pharmaceutically active components.

In one embodiment the composition is lyophilized.

In one embodiment of the instant invention, the liquid compositions can be filled into lyo-vials and subsequently lyophilized. Lyophilisation of the samples is conducted by freezing the samples at temperatures between −35° C. to −65° C. for a period of from 1 to 10 hours, e.g. 5 to 10 hours. This step is followed by primary drying at a shelf temperature of −30° C. to 10° C., e.g. −20° C. to 10° C. or 5° C. to 10° C. under a pressure of 100 mTorr to 200 mTorr for a period of 10 hours to 25 hours. Finally, the samples enter the last step of the lyophilisation process, being secondary drying, which is conducted at a shelf temperature of 15° C. to 25° C. for 5 hours to 15 hours. Sample volume in the lyo-vials varies between 0.1 to 5 ml, e.g. 0.2 to 1 ml or 0.4 to 0.6 ml, or 0.5 ml. In one embodiment sample volume is between 2 ml to 4 ml.

In one further embodiment of the present invention, the lyophilisation process can be conducted by freezing the samples at a shelf temperature of −45° C. for about 2 hours followed by primary drying at a shelf temperature of −25° C. and 90 mTorr for 12 hours, and secondary drying at a shelf temperature of 25° C. for 12.5 hours.

In one embodiment an injectable solution comprising the said composition is claimed.

The injectable solution claimed herein is stable at a temperature of 2 to 8° C. for 24 hours.

In one embodiment said injectable solution is obtained by reconstituting said lyophilised composition with a pharmaceutically acceptable sterile solvent prior to administration to a mammal.

In one further embodiment, the present invention relates to a process for the preparation of said injectable solution designed for intravenous, subcutaneous, intramuscular, intraarticular, intraperitoneal, intracerobrospinal, intracardiac, intrathecal, intravesical, intraosseous, intravitreal, epidural, intrasynovial injection into a mammal. Said process comprises the step of dissolving the said lyophilised composition as claimed herein, prior to administration, in a pharmaceutical acceptable sterile solvent.

In another embodiment of the instant invention, said injectable solution is also administered via other routes of administration. Such routes of administration are, but not limited to, inhalation, oral and nasal. An example for such an application is, but not limited to, for instance, inhalation of α-1 Antitrypsin by COPD patients in form of an injectable solution as claimed herein.

The composition as claimed herein is for use as a medicament, a cosmetic product, a cosmoceutical product or a diagnostic product.

The term "medicament" as used herein relates to a product or a mixture of products, wherein said products may be mixed prior to administration or be used one after another and have a therapeutical and/or diagnostic outcome on the mammal they are administered to.

The term "cosmetic product" as used herein relates to products employed for cosmetic purposes. The term "cosmetic" as used herein relates to products as defined in the FD&C Act, sec. 201(i) (*Federal Food, Drug and Cosmetic Act, FDA*) as intended to be rubbed, poured, sprinkled, or sprayed on, introduced into, or otherwise applied to the human body for cleansing, beautifying, promoting attractiveness, or altering the appearance".

The term "diagnostic product" as used herein relates to any product comprising any compound or compounds that is delivered to a patient in order to carry out a diagnostic test or assay on the patient.

The term "cosmeceutical product" as used herein relates to a non-prescription cosmetic product, that has also medicinal or drug-like benefits.

In one embodiment of the present invention the claimed formulation herein may comprise a buffer.

The term "buffer" as used herein relates to an aqueous solution consisting of a mixture of a weak acid and its conjugate base or a weak base and its conjugate acid.

In one further embodiment of the present invention the buffer is selected from the group consisting of phosphate buffer, acetate buffer, citrate buffer, formate buffer, benzoate buffer, TRIS (Tris(hydroxymethyl)-aminomethan) and maleate buffer. Said buffer is prepared according to the specifications of USP (United States Pharmacopoeia), EP (European Pharmacopoeia) and the JP (Japanese Pharmacopoeia) by using Pharmacopoeia-conform excipients. The buffer concentration is to be determined in regard to the pH of the end product.

The excipients and the actives (peptides and/or proteins) employed in the formulation herein are pharmaceutically acceptable.

The term "pharmaceutically acceptable" as used herein relates to any excipient, pharmaceutically active ingredient, which enables the said composition to be taken by mammals at therapeutically effective concentration, avoiding any kind of side effects.

In one aspect the present invention pertains to a kit comprising one or more containers comprising the formulation/composition and instructions for use of the formulation/composition and optionally a pharmaceutically acceptable sterile solvent.

The term "solvent" as used herein relates to any liquid which aids in dissolving or diluting any other substance or substance mixture or a product. The term "solvent" within the meaning of the instant invention may encompass also a mixture of solvents.

The pharmaceutical acceptable sterile solvent to be employed within said process is, but not limited to, water for injection (WFI), isotonic salt solution, Ringer's solution, pH-buffered solution, an aqueous solution of 5% glucose.

A further aspect of the present invention relates to a sterile composition.

The term "sterile" as used herein relates to the absence of undesired microorganisms and relates to the norms defined in the USP (United States Pharmacopoeia), EP (European Pharmacopoeia) and the JP (Japanese Pharmacopoeia).

In one embodiment the composition is non-pyrogenic e.g. containing <1 EU (endotoxin unit, a standard measure) per dose, and preferably <0.1 EU per dose. In one further embodiment said injectable solution is also sterile and non-pyrogenic.

In one embodiment of the instant invention said composition is for use in vertebrates, such as mammals.

The term "Vertebrate" is defined herein as any member of the subphylum vertebrata, chordates with backbones or spinal columns. Therefore the term "vertebrate" encompasses humans, mammals, marsupials, reptiles, birds, amphibians and fish.

The term "mammal" in this document is defined as any warm-blooded, vertebrate characterized by the presence of sweat glands, including milk producing glands, and by the presence of hair, three middle ear bones used in hearing, and a neocortex region in the brain. A male or female human, dog, cat, pig, cow, horse, donkey, sheep, goat and deer is therefore encompassed by this definition of a mammal.

The term "marsupial" is defined herein as a mammal in which the female typically has a pouch in which it rears its young through early infancy. They differ from placental mammals in their reproductive traits.

The term "reptile" is defined herein as any air-breathing, ectothermic vertebrate that has skin covered in scales as opposed to hair or feathers.

The term "bird" is defined herein as any bipedal, warm-blooded, vertebrate that lays eggs.

The term "amphibian" is defined herein as all living tetrapods (four-legged vertebrates) that do not have amniotic eggs, are ectothermic and generally spend part of their time on land.

The term "fish" is defined herein as aquatic vertebrates that are typically ectothermic, covered with scales, and equipped with two sets of paired fins and several unpaired fins.

The concentration values herein are expressed in "about" values.

The term "about" as used herein is intended to reflect a variation of 20% of the value it is attached to.

The instant invention further relates to a process for preparing the said composition characterized in that said composition is prepared as an aqueous composition and subsequently lyophilized.

Prior to lyophilisation, the protein or peptide is dissolved in an aqueous solution, which is stabilized by a hydrophilic polymer, a mixture of polyalcohol and a sugar, a detergent. The stabilization of the protein in solution means that the protein is enveloped by a structure composed of hydrophilic polymer, a detergent and a mixture of polyalcohol and sugar.

By using a detergent, it is possible to reduce the amount of hydrophilic polymers. In one embodiment by using Tween 80 the concentration of PVP was reduced from 150 mg/g to 80 mg/g based on the total weight of production bulk composition. Due to such an effect, the industrial production of the composition herein was improved.

In one embodiment of the present invention the composition herein comprises the neurotoxic component of *Botulinum* toxin in a quantity of about 2 pg to 50 ng per 1 g production bulk composition. Preferred quantity ranges are in the range of from 2 pg to 200 pg, 200 pg to 400 pg, 400 pg to 600 pg, 600 pg to 800 pg, 800 pg to 1 ng, 1 ng to 1.5 ng, 1.5 ng to 2 ng, 2 ng to 2.5 ng, 2.5 ng to 3 ng, 3 to 3.5 ng, 3.5 to 4 ng, 4 ng to 4.5 ng, and 4.5 to 5 ng per 1 g of water, respectively per 1 g production bulk composition. In an embodiment of the instant invention, the neurotoxic component has a biological activity of 50 to 250 $LD_{50}$ units per ng neurotoxic component, as determined in a mouse $LD_{50}$ assay. In one further embodiment, the neurotoxic component has a biological activity of about 150 $LD_{50}$ per ng neurotoxic component.

The following demonstrates some embodiments of the stable compositions as claimed herein, wherein the amounts of the constituents specified are all relative to 1 g production bulk composition.

In one further embodiment of the present invention, the composition claimed herein comprises ≤1.6 ng neurotoxic component of *Botulinum* toxin, about 0.5 mg of hyaluronic acid, about 15.0 mg of mannitol, about 5.0 mg of sucrose and about 0.1 mg of Polysorbate 80.

In another embodiment of the present invention, the composition claimed herein comprises ≤1.6 ng neurotoxic component of *Botulinum* toxin, about 1.0 mg of hyaluronic acid, about 30.0 mg of mannitol, about 10.0 mg of sucrose and about 0.2 mg of Polysorbate 80.

In another embodiment of the present invention, the composition claimed herein comprises ≤1.6 ng neurotoxic component of *Botulinum* toxin, about 2.0 mg of hyaluronic acid, about 40.0 mg of mannitol, about 10.0 mg of sucrose and about 0.5 mg of Polysorbate 80.

In another embodiment of the present invention, the composition claimed herein comprises ≤1.6 ng neurotoxic component of *Botulinum* toxin, about 2.0 mg of hyaluronic acid, about 40.0 mg of mannitol, about 10.0 mg of sucrose and about 0.2 mg of Polysorbate 80.

In one further embodiment of the present invention, the composition claimed herein comprises ≤1.6 ng neurotoxic component of *Botulinum* toxin, about 1.0 mg of hyaluronic acid, about 40.0 mg of mannitol, about 10.0 mg of sucrose and about 0.5 mg of Polysorbate 80.

In one further embodiment of the present invention, the composition claimed herein comprises ≤1.6 ng neurotoxic component of *Botulinum* toxin, about 1.0 mg of hyaluronic acid, about 10.0 mg of sucrose and about 0.2 mg of Polysorbate 80.

In one further embodiment of the present invention, the composition claimed herein comprises ≤1.6 ng neurotoxic component of *Botulinum* toxin, about 80.0 mg of polyvinylpyrrollidone (PVP), about 50 mg of mannitol, and about 0.2 mg of Polysorbate 80.

In one further embodiment of the present invention, the composition claimed herein comprises ≤1.6 ng neurotoxic component of *Botulinum* toxin, about 80.0 mg of polyvinylpyrrollidone (PVP), about 50 mg of mannitol, and about 0.5 mg of Polysorbate 80.

In one further embodiment of the present invention, the composition claimed herein comprises ≤1.6 ng neurotoxic component of *Botulinum* toxin, about 100.0 mg of polyvinylpyrrollidone (PVP), about 30.0 mg of mannitol, about 10.0 mg of sucrose and about 0.2 mg of Polysorbate 80.

In one further embodiment of the present invention, the composition claimed herein comprises ≤1.6 ng neurotoxic component of *Botulinum* toxin, about 80.0 mg of polyvinylpyrrollidone (PVP), about 30.0 mg of mannitol, about 10.0 mg of sucrose and about 0.2 mg of Polysorbate 80.

In one further embodiment of the present invention, the composition claimed herein comprises ≤1.6 ng neurotoxic component of *Botulinum* toxin, about 80.0 mg of polyvinylpyrrollidone (PVP), about 30.0 mg of mannitol, about 10.0 mg of sucrose about 0.2 mg of Polysorbate 80 and about 10 mM phosphate buffer (pH 7.4).

In one further embodiment of the present invention, the composition claimed herein comprises ≤1.6 ng neurotoxic component of *Botulinum* toxin, about 50.0 mg of polyvinylpyrrollidone (PVP), about 30.0 mg of mannitol, about 10.0 mg of sucrose about 0.2 mg of Polysorbate 80 and about 10 mM phosphate buffer (pH 7.4).

In one further embodiment of the present invention, the composition claimed herein comprises ≤1.6 ng neurotoxic component of *Botulinum* toxin, about 100.0 mg of polyvinylpyrrollidone (PVP), about 30.0 mg of mannitol, about 10.0 mg of sucrose and about 0.5 mg of Polysorbate 80.

In one further embodiment of the present invention, the composition claimed herein comprises ≤1.6 ng neurotoxic component of *Botulinum* toxin, about 100.0 mg of polyvinylpyrrollidone (PVP), about 50.0 mg of mannitol, and about 0.2 mg of Polysorbate 80.

In one further embodiment of the present invention, the composition claimed herein comprises ≤1.6 ng neurotoxic component of *Botulinum* toxin, about 100.0 mg of polyvinylpyrrollidone (PVP), about 50.0 mg of mannitol, and about 0.5 mg of Polysorbate 80.

In one further embodiment of the present invention, the composition claimed herein comprises ≤1.6 ng neurotoxic component of *Botulinum* toxin, about 150.0 mg of polyvinylpyrrollidone (PVP), about 30.0 mg of mannitol, about 10.0 mg of sucrose and about 0.2 mg of Polysorbate 80.

Composition as claimed herein is for treatment of a disease or condition caused by or associated with hyperactive cholinergic innervation of muscles or exocrine glands in a patient, where the neurotoxic component blocks acetylcholine secretion into the synaptic cleft. Therefore, the composition claimed by the present invention may be directed to the treatment of any of the following indications, most of which are described in detail in Dressler D (2000) (*Botulinum* Toxin Therapy. Thieme Verlag, Stuttgart, N.Y.):

dystonia
  cranial dystonia
  blepharospasm
  oromandibular dystonia
    jaw opening type
    jaw closing type
  bruxism
  Meige syndrome
  lingual dystonia
  apraxia of eyelid opening
  cervical dystonia
  antecollis
  retrocollis
  laterocollis
  torticollis
  pharyngeal dystonia
  laryngeal dystonia
  spasmodic dysphonia/adductor type
  spasmodic dysphonia/abductor type
  spasmodic dyspnea
  limb dystonia
  arm dystonia
    task specific dystonia
      writer's cramp
      musician's cramps
      golfer's cramp
  leg dystonia
    thigh adduction, thigh abduction
    knee flexion, knee extension ankle flexion, ankle extension
equinovarus deformity
foot dystonia
striatal toe
toe flexion
toe extension
axial dystonia
pisa syndrome
belly dancer dystonia
segmental dystonia
hemidystonia
generalised dystonia
dystonia in lubag
dystonia in corticobasal degeneration
dystonia in lubag
tardive dystonia
dystonia in spinocerebellar ataxia
dystonia in Parkinson's disease
dystonia in Huntington's disease
dystonia in Hallervorden Spatz disease
dopa-induced dyskinesias/dopa-induced dystonia
tardive dyskinesias/tardive dystonia
paroxysmal dyskinesias/dystonias
kinesiogenic
non-kinesiogenic
action-induced
palatal myoclonus
myoclonus
myokymia
rigidity
benign muscle cramps
hereditary chin trembling
paradoxic jaw muscle activity
hemimasticatory spasms
hypertrophic branchial myopathy
maseteric hypertrophy
tibialis anterior hypertrophy
nystagmus
oscillopsia
supranuclear gaze palsy
epilepsia partialis continua
planning of spasmodic torticollis operation
abductor vocal cord paralysis
recalcitant mutational dysphonia
upper oesophageal sphincter dysfunction
vocal fold granuloma
stuttering
Gilles de la Tourette syndrome
middle ear myoclonus
protective larynx closure
postlaryngectomy speech failure
protective ptosis
entropion
sphincter Odii dysfunction
pseudoachalasia
nonachalsia oesophageal motor disorders
vaginismus
postoperative immobilisation
tremor
bladder dysfunction
detrusor sphincter dyssynergia
bladder sphincter spasm
hemifacial spasm
reinnervation dyskinesias
cosmetic use
craw's feet
frowning
facial asymmetries
mentalis dimples
stiff person syndrome
tetanus
prostate hyperplasia
adipositas treatment
infantile cerebral palsy
strabismus
mixed
paralytic
concomitant
after retinal detachment surgery
after cataract surgery
in aphakia
myositic strabismus
myopathic strabismus
dissociated vertical deviation
as an adjunct to strabismus surgery
esotropia
exotropia
achalasia
anal fissures
exocrine gland hyperactivity
Frey syndrome
Crocodile Tears syndrome
hyperhidrosis
axillar
palmar
plantar
rhinorrhea
relative hypersalivation
in stroke
in parkinsosn's
in amyotrophic lateral sclerosis
spastic conditions
in encephalitis and myelitis
autoimmune processes
multiple sclerosis
transverse myelitis
Devic syndrome
viral infections
bacterial infections
parasitic infections
fungal infections
in hereditary spastic paraparesis
postapoplectic syndrome
hemispheric infarction
brainstem infarction
myelon infarction
in central nervous system trauma
hemispheric lesions
brainstem lesions
myelon lesion
in central nervous system hemorrhage
intracerebral hemorrhage
subarachnoidal hemorrhage
subdural hemorrhage
intraspinal hemorrhage
in neoplasias
hemispheric tumors
brainstem tumors
myelon tumors In another embodiment, the present invention pertains to a kit, wherein said kit comprises one or more of a container comprising the formulation/composition claimed herein, instructions for reconstituting the said formulation/composition and optionally, a pharmaceutically acceptable sterile solvent. Suitable containers include, but are not limited to, single vials, dual chamber vials, single application syringes or dual chamber syringes. The container may be formed from a variety of material such as glass or plastic adapted for pharmaceutical, diagnostic, cosmetic or cosmeceutical administration. The said kit may be adapted for single use or for multiple uses.

The invention is now described with reference to the following examples. These examples are provided for the purpose of illustration only and the invention should not be construed as being limited to these examples, but rather should be construed to encompass any and all variations which become evident as a result of the teaching provided herein. The following materials and methods are provided with respect to the subsequent examples but do not limit a multiplicity of materials and methodologies encompassed by the present invention.

EXAMPLES

Examples

Studies were conducted to find a stabilized composition of *Botulinum* toxin type A. Each composition comprised of ≤1.6 ng neurotoxic component of *Botulinum* toxin type A. The composition of the screening formulations is summarized in the following table, wherein the amounts are given as mg per 1 g of the production bulk composition.

| Formulation No | PVP [mg/g] | Hyaluronic acid [mg/g] | Mannitol [mg/g] | Sucrose [mg/g] | Polysorbate 80 [mg/g] |
|---|---|---|---|---|---|
| Comparative Formulation 1 | 100 | — | 50 | — | 0.5 |
| Comparative Formulation 2 | — | 1 | 30 | 10 | — |
| Comparative Formulation 3 | — | — | 30 | 10 | 0.2 |
| Example 1 | 80 | — | 30 | 10 | 0.2 |
| Example 2 | — | 2 | 40 | 10 | 0.5 |
| Example 3 | — | 2 | 30 | 10 | 0.2 |
| Example 4 | — | 1 | 30 | 10 | 0.2 |

| Formulation No | Start Value | 40° C./75% RH 1 Month | 40° C./75% RH 3 Months | 40° C./75% RH 7 Months |
|---|---|---|---|---|
| | | T½ [min] | | |
| Comparative Formulation 1 | 68 | 76 | 98 | n.m. |
| Comparative Formulation 2 | 138 | 110 | n.m. | n.m. |
| Comparative Formulation 3 | 96 | n.m. | n.m. | n.m. |
| Example 1 | 67 | 72 | 87 | 90 |
| Example 2 | 66 | 85 | n.m. | n.m. |
| Example 3 | 69 | 78 | n.m. | n.m. |
| Example 4 | 68 | 69 | n.m. | 67 | n.m. = not measured

| Formulation No | Start Value | 25° C./60% RH 1 Month | 25° C./60% RH 3 Months | 25° C./60% RH 7 Months |
|---|---|---|---|---|
| | | T½ [min] | | |
| Example 1 | 67 | 69 | 75 | n.m. |
| Example 4 | 71 | 64 | 74 | 66 |

The stability of the formulations were determined by using a HDA-assay as defined by Göschel et al. ("*Botulinum Toxin Therapy: Neutralizing and Nonneutralizing Antibodies—Therapeutic Consequences*" Experimental Neurology, 1997; 147: 96-102). The start value was measured after lyophilisation. The mean of all four experiments is calculated and compared to the data generated by the reference material. The change of paralysis time over time of storage indicates the stability of the neurotoxin formulation: increasing of sample paralysis time compared to original values indicate a loss of activity of neurotoxin.

The results are expressed in minutes required to reach half of the initial muscle concentration force. Shorter time valves reflect higher amounts of active toxin. The results can be interpreted as follows: In principle the formulations according to the present invention are more stable compared to the Comparative Formulations, wherein one of the constituents required is missing.

It becomes apparent from Comparative Formulation 1, in the absence of sucrose, a formulation with an active toxin may be prepared, which, however, looses rapidly its activity such that within 3 months at 40° C. and 75% RH the activity of the toxin is significantly reduced. Comparative Formulation 2 shows that in absence of the detergent, the toxin significantly looses activity already during production, as becomes apparent from the high starting value of 138 min directly measured after lyophilization. Comparative Formulation 3 shows that in absence of the hydrophilic polymer, the toxin significantly looses activity already during production, as becomes apparent from the high starting value of 96.

The invention claimed is:

1. A formulation consisting essentially of:
   (a) hyaluronic acid,
   (b) a mixture of a polyalcohol and a sugar, and wherein the weight ratio of polyalcohol to sugar is from 2:1 to 5:1 (wt-%),
   (c) a surfactant, and
   (d) a *Clostridium botulinum* toxin,
wherein the formulation is free of human serum albumin (HSA), gelatin, histidine, lysine, methionine immunoglobulins.

2. The formulation of claim 1, wherein the polyalcohol is selected from mannitol, inositol, lactilol, isomalt, xylitol, erythritol, sorbitol, and mixtures thereof.

3. The formulation of claim 1, wherein the sugar is selected from monosaccharides, disaccharides, polysaccharides, and mixtures thereof.

4. The formulation of claim 1, which is lyophilized.

5. The formulation of claim 1, which comprises *Clostridium botulinum* toxin, hyaluronic acid, mannitol, sucrose, polysorbate 80 and, optionally, water for injection.

6. An injectable solution comprising the formulation of claim 1.

7. The formulation of claim 1, in the form of a cosmetic product, a cosmeceutical product or a diagnostic product.

8. The formulation of claim 1, comprising a therapeutically effective amount of the *Clostridium botulinum* toxin for the treatment of a disease or condition caused by or associated with hyperactive cholinergic innervation of muscles or exocrine glands in a patient.

9. A kit comprising
   (a) one or more containers comprising the formulation of claim 1, and
   (b) instructions for use of the formulation of claim 1, and optionally,
   (c) a pharmaceutically acceptable sterile solvent.

* * * * *

UNITED STATES PATENT AND TRADEMARK OFFICE
CERTIFICATE OF CORRECTION

PATENT NO.        : 9,198,856 B2                                      Page 1 of 1
APPLICATION NO.   : 13/138884
DATED             : December 1, 2015
INVENTOR(S)       : Markus Burger et al.

It is certified that error appears in the above-identified patent and that said Letters Patent is hereby corrected as shown below:

Title Page, Item 56: "Russian application No. 201146541/15(069722)" should be
--Russian application No. 2011146541/15(069722)--.

Signed and Sealed this
Twenty-sixth Day of January, 2016

Michelle K. Lee
*Director of the United States Patent and Trademark Office*